(12) United States Patent
Shifflette

(10) Patent No.: US 8,388,565 B2
(45) Date of Patent: Mar. 5, 2013

(54) APPARATUS COMPRISING A DRIVE CABLE FOR A MEDICAL DEVICE (II)

(75) Inventor: J. Michael Shifflette, Alachua, FL (US)

(73) Assignee: NuCardia, Inc., El Dorado Hills, CA (US)

(*) Notice: Subject to any disclaimer, the term of this patent is extended or adjusted under 35 U.S.C. 154(b) by 168 days.

(21) Appl. No.: 12/910,633

(22) Filed: Oct. 22, 2010

(65) Prior Publication Data

US 2011/0040140 A1    Feb. 17, 2011

Related U.S. Application Data

(63) Continuation of application No. 11/758,402, filed on Jun. 5, 2007, now Pat. No. 7,828,710.

(51) Int. Cl.
*A61B 17/32* (2006.01)

(52) U.S. Cl. ............ 604/6.11; 600/16; 604/16; 604/151

(58) Field of Classification Search .................... 600/16; 604/16, 151, 6.11
See application file for complete search history.

(56) References Cited

U.S. PATENT DOCUMENTS

| | | |
|---|---|---|
| 4,625,712 A | 12/1986 | Wampler |
| 4,686,982 A | 8/1987 | Nash |
| 4,753,221 A | 6/1988 | Kensey |
| 4,817,586 A | 4/1989 | Wampler |
| 4,846,152 A | 7/1989 | Wampler et al. |
| 4,919,647 A | 4/1990 | Nash |
| 4,969,865 A | 11/1990 | Hwang |
| 5,092,844 A | 3/1992 | Schwartz et al. |
| 5,163,910 A | 11/1992 | Schwartz et al. |
| 5,169,378 A | 12/1992 | Figuera |
| 5,376,114 A | 12/1994 | Jarvik |
| 5,405,383 A | 4/1995 | Barr |
| 5,488,761 A | 2/1996 | Leone |
| 5,588,812 A | 12/1996 | Taylor et al. |
| 5,749,855 A | 5/1998 | Reitan |
| 5,755,784 A | 5/1998 | Jarvik |
| 5,776,190 A | 7/1998 | Jarvik |
| 5,888,241 A | 3/1999 | Jarvik |
| 6,007,478 A | 12/1999 | Siess et al. |
| 6,053,907 A | 4/2000 | Zirps |
| 6,053,922 A | 4/2000 | Krause et al. |
| 6,058,593 A | 5/2000 | Siess |
| 6,135,943 A | 10/2000 | Yu et al. |
| 6,139,487 A | 10/2000 | Siess |

(Continued)

FOREIGN PATENT DOCUMENTS

| | | |
|---|---|---|
| WO | 9639956 A1 | 12/1996 |
| WO | 0121249 A1 | 3/2001 |

(Continued)

OTHER PUBLICATIONS

Siegenthaler et al., "The Impella Recover microaxial left ventricular assist device reduces mortality for postcardiotomy failure: . . . ", "The Journal of Thoracic and Cardiovascular Surgery—Evolving Technology", Mar. 2004, pp. 812-822, Publisher: The American Association for Thoracic Surgery.

(Continued)

*Primary Examiner* — Carl H Layno
*Assistant Examiner* — Natasha Patel
(74) *Attorney, Agent, or Firm* — Kaplan Breyer Schwarz & Ottesen, LLP

(57) ABSTRACT

An article comprising a drive cable suitable for high-speed operation in an anatomy having small-radii bends is disclosed. The drive cables disclosed herein include one or more physical adaptations that enable them to be "tuned" to avoid large amplitude vibrations during operation.

15 Claims, 7 Drawing Sheets

U.S. PATENT DOCUMENTS

| | | |
|---|---|---|
| 6,176,822 B1 | 1/2001 | Nix et al. |
| 6,176,848 B1 | 1/2001 | Ran et al. |
| 6,200,260 B1 | 3/2001 | Bolling |
| 6,227,820 B1 | 5/2001 | Jarvik |
| 6,245,007 B1 | 6/2001 | Bedingham et al. |
| 6,295,877 B1 | 10/2001 | Aboul-Hosn et al. |
| 6,299,575 B1 | 10/2001 | Bolling |
| 6,387,037 B1 | 5/2002 | Bolling et al. |
| 6,390,969 B1 | 5/2002 | Bolling et al. |
| 6,406,422 B1 | 6/2002 | Landesberg |
| 6,428,464 B1 | 8/2002 | Bolling |
| 6,497,698 B1 | 12/2002 | Fonger et al. |
| 6,508,787 B2 | 1/2003 | Erbel et al. |
| 6,527,699 B1 | 3/2003 | Goldowsky |
| 6,533,716 B1 | 3/2003 | Schmitz-Rode et al. |
| 6,544,216 B1 | 4/2003 | Sammler et al. |
| 6,620,004 B1 | 9/2003 | Piper |
| 6,623,475 B1 | 9/2003 | Siess |
| 6,644,125 B1 | 11/2003 | Siess et al. |
| 6,685,621 B2 | 2/2004 | Bolling et al. |
| 6,685,696 B2 | 2/2004 | Fleischhacker et al. |
| 6,716,157 B2 | 4/2004 | Goldowsky |
| 6,719,720 B1 | 4/2004 | Voelker et al. |
| 6,790,171 B1 | 9/2004 | Griindeman et al. |
| 6,794,789 B2 | 9/2004 | Siess et al. |
| 6,808,483 B1 | 10/2004 | Ortiz et al. |
| 6,889,082 B2 | 5/2005 | Bolling et al. |
| 6,942,611 B2 | 9/2005 | Siess |
| 6,981,942 B2 | 1/2006 | Khaw et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,027,875 B2 | 4/2006 | Siess et al. |
| 7,070,555 B2 | 7/2006 | Siess |
| 7,258,679 B2 | 8/2007 | Moore et al. |
| 7,371,210 B2 | 5/2008 | Brock et al. |
| 7,393,181 B2 | 7/2008 | McBride et al. |
| 2003/0105383 A1 | 6/2003 | Barbut et al. |
| 2003/0163019 A1 | 8/2003 | Goldowsky |
| 2004/0006358 A1 | 1/2004 | Wulfman et al. |
| 2004/0241019 A1 | 12/2004 | Goldowsky |
| 2005/0049696 A1 | 3/2005 | Siess |
| 2005/0054950 A1 | 3/2005 | Parins |
| 2006/0008349 A1 | 1/2006 | Khaw |
| 2008/0103591 A1 | 5/2008 | Siess |
| 2008/0114339 A1 | 5/2008 | McBride et al. |

FOREIGN PATENT DOCUMENTS

| | | |
|---|---|---|
| WO | 0139817 A2 | 6/2001 |
| WO | 0174419 A1 | 10/2001 |
| WO | 0241935 A1 | 5/2002 |
| WO | 0243791 A1 | 6/2002 |
| WO | 0245775 A2 | 6/2002 |

OTHER PUBLICATIONS

Veronique Van Loon-Megard, "PCT/US2008/065779 International Search Report", Jan. 22, 2009, Publisher: EPO, Published in: EP.

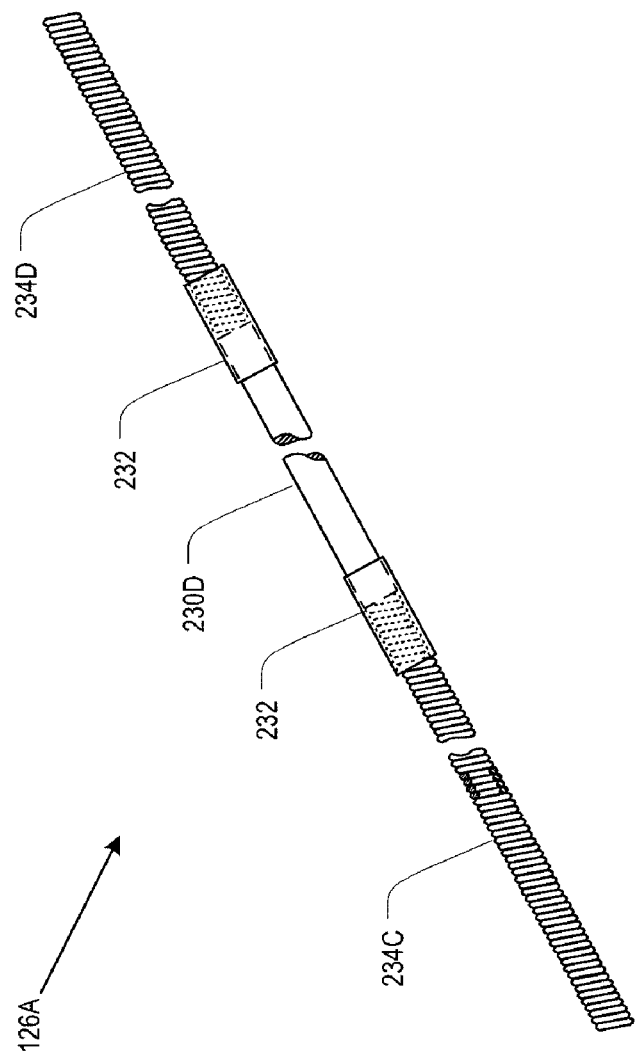

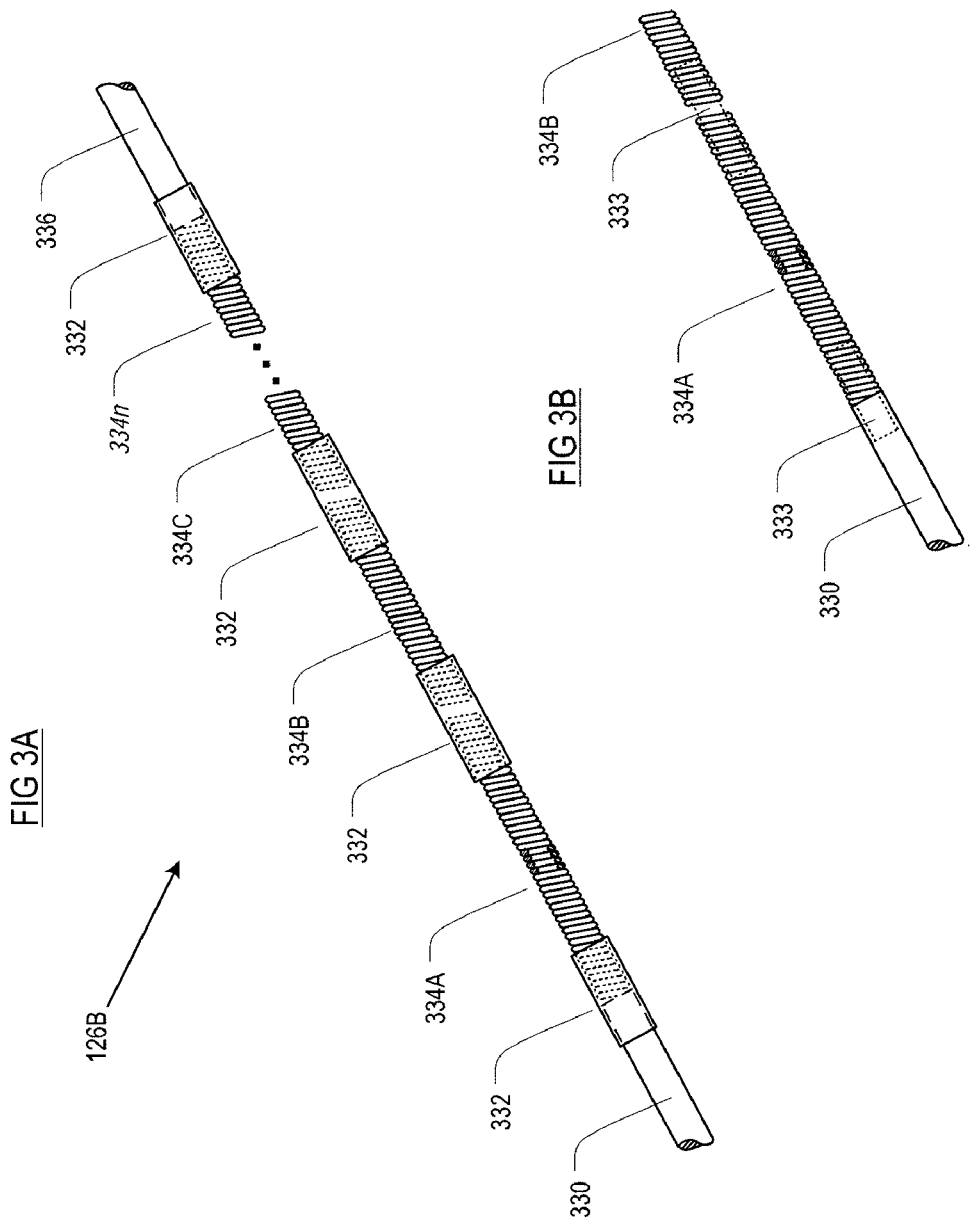

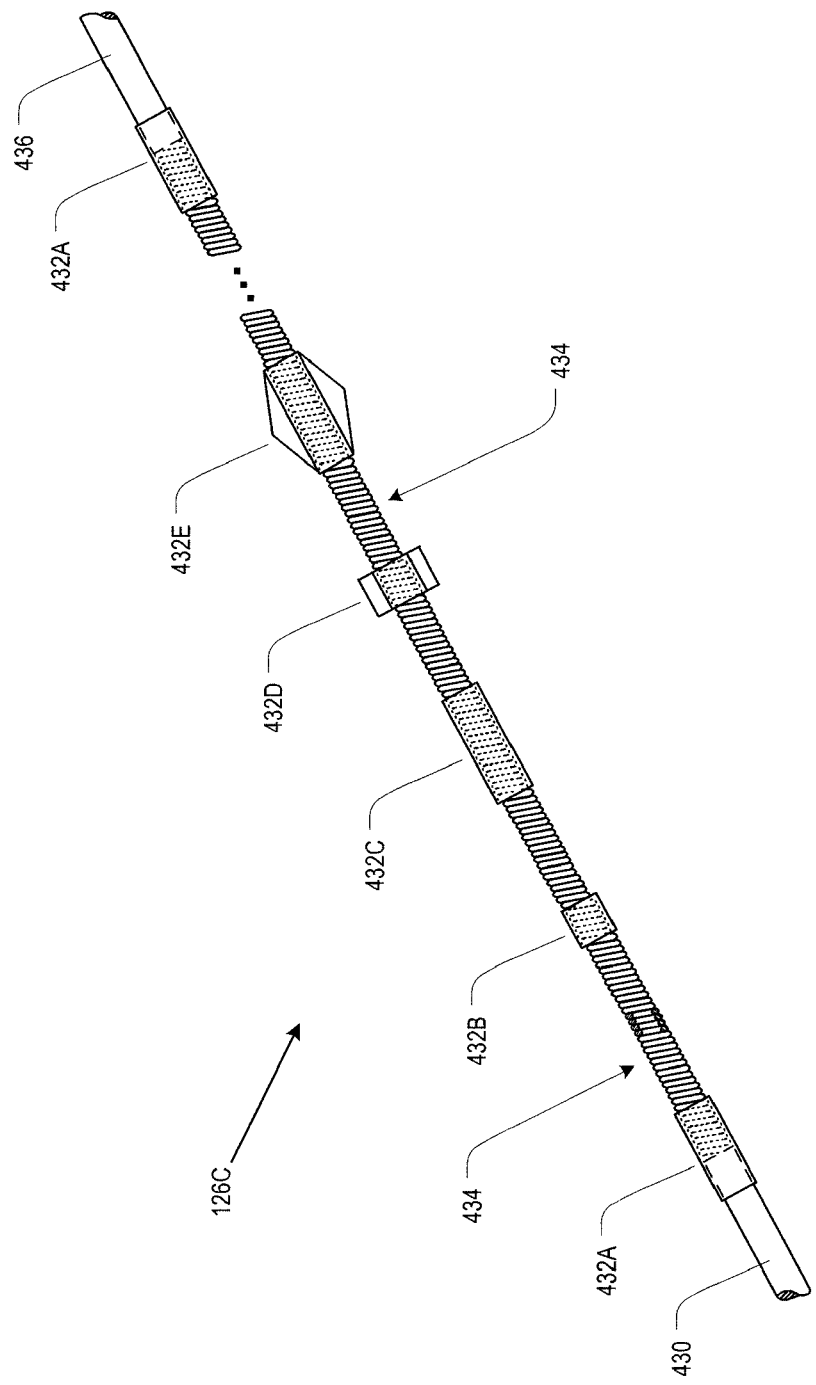

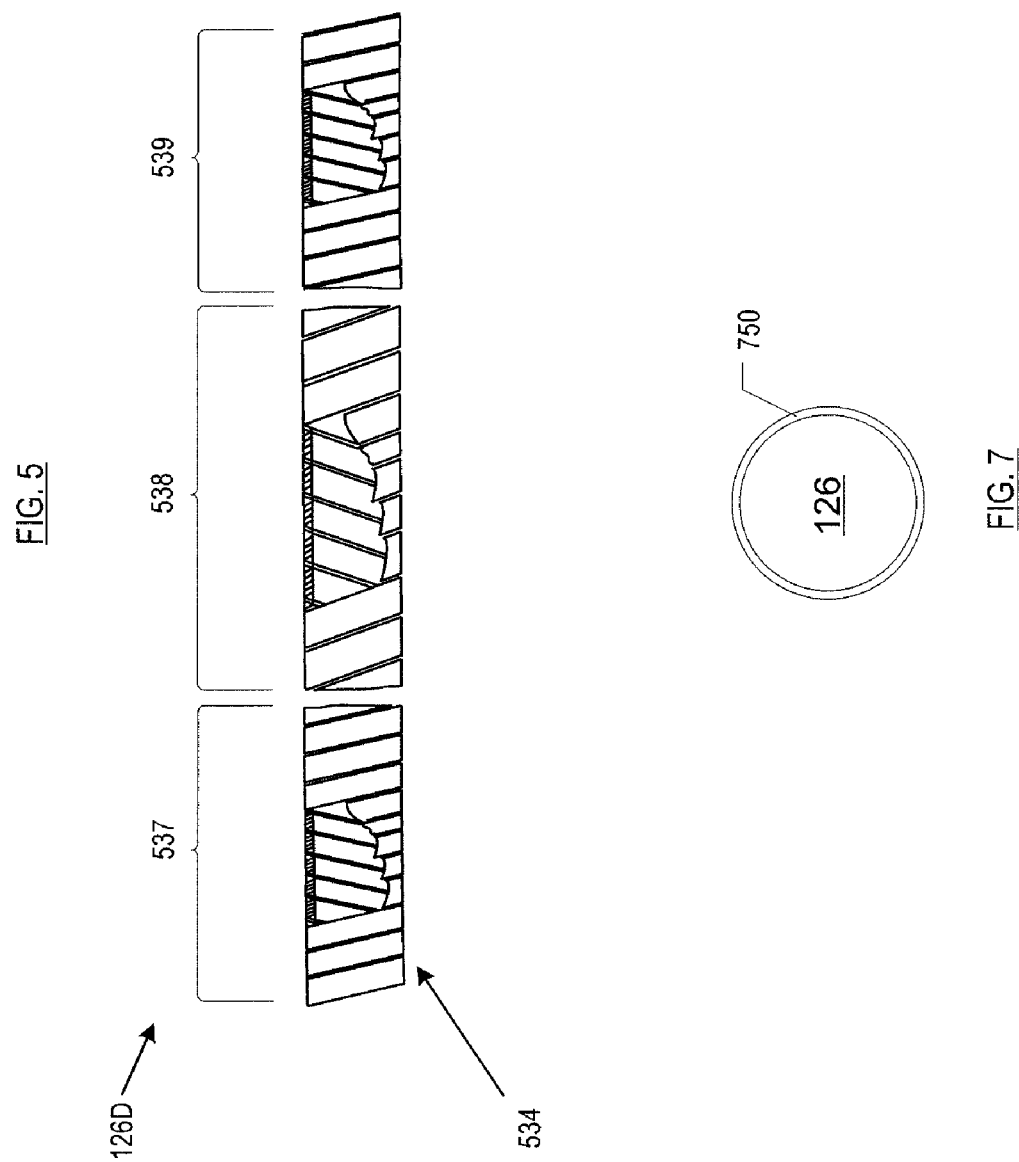

APPARATUS COMPRISING A DRIVE CABLE FOR A MEDICAL DEVICE (II)

CROSS REFERENCE TO RELATED APPLICATIONS

This case is a continuation of U.S. patent application Ser. No. 11/758,402 filed Jun. 5, 2007. The following cases are incorporated by reference herein:
  (1) U.S. Published Patent Application US 2008 0132747-A1; and
  (2) U.S. Published Patent Application US 2008 0132748-A1.
  (3) U.S. patent application Ser. No. 11/758,402, now U.S. Pat. No. 7,828,710, filed Jun. 5, 2007.

If there are any contradictions or inconsistencies in language between this application and one or more of the cases that have been incorporated by reference that might affect the interpretation of the claims in this case, the claims in this case should be interpreted to be consistent with the language in this case.

FIELD OF THE INVENTION

The present invention relates to drive cables, including those suitable for use in conjunction with a blood pump or other medical device.

BACKGROUND OF THE INVENTION

Acute heart failure is the sudden inability of the heart to fill with or pump a sufficient volume of blood. The afflicted patient may become weak and short of breath and, in some instances, die. In the most severe acute heart-failure episodes, a patient experiences cardiogenic shock, a condition that is associated with high reported mortality rates.

Acute heart failure occurs in a variety of contexts. For example, some patients who are hospitalized for Acute Coronary Syndrome (i.e., heart attack and unstable angina) develop acute heart failure. Furthermore, some open-heart surgery patients develop acute heart failure. Acute heart failure also complicates certain illnesses. Additionally, some patients who undergo a Percutaneous Coronary Intervention or other procedure are at risk for developing acute heart failure or dying.

Acute heart failure does not necessarily progress to chronic heart failure or death; recovery is possible. Many patients who have acute heart failure and those at risk for developing it receive interventions that are intended to temporarily assist the heart during a recovery period. The intervention typically lasts for less than a week, but may last longer.

These interventions may include pharmaceuticals and medical devices, including cardiac-assist devices. When these cardiac-assist devices include a pump that supplements the heart's pumping action, they often are referred to as "blood pumps." An effective cardiac-assist device assumes some of the heart's pumping function, thereby unloading the heart and enabling it to recover. Cardiac-assist devices and blood pumps can be temporary or permanent.

Over the years, various types of temporary blood pumps have been developed. One type of temporary blood pump is the catheter blood pump. This type of blood pump has a cable-driven rotor that is attached to a catheter. The catheter is inserted into a peripheral vessel, such as the femoral artery, and is then typically advanced to the aorta.

The catheter encloses a rotating drive cable that couples to impeller blades at one end. The other end of the drive cable couples to an extracorporeal motor. As the motor turns, the drive cable rotates, thereby conveying motor torque through the length of the catheter to the impeller blades. This causes the impeller to rotate at high speed, usually in the range of about 1000 to about 100,000 rpm. The impeller's rotation induces a flow of blood through the pump.

One of the more problematic components of the catheter blood pump is the drive cable/catheter assembly. Among other issues for concern, it is very difficult to provide a drive cable/catheter assembly that:
  is capable of rotating at the required speeds; and
  has the flexibility to negotiate small-radii bends, such as the aortic arch, as occur in the vascular system; and
  is able to maintain structural integrity for a clinically relevant duration (e.g., hours to weeks, etc.) at operating speed.

Flexible drive cables currently exist; a common example is an automobile speedometer cable. But these cables operate at gentle curvature and low speed; they are not suitable for use at higher speeds in geometries having small-radii bends.

Rods (solid or hollow) are suitable for transmitting torque at high rpm, but only if the rod is relatively straight. A rod is too stiff to spin in an arc; it will soon fracture and fail. Failure occurs even if the rod is constructed of a super-elastic material, such as Nitinol.

Coils are better suited than solid rods for high-speed operation over small-radii bends. In fact, coils are currently available for transmitting torque "around corners" for long-length applications. But manufacturers normally limit these coils to maximum operating speeds of about 20,000 rpm. As previously mentioned, catheter blood pumps often operate at rotational speeds well in excess of 20,000 rpm. In fact, in some instances, rotational speeds of up to 100,000 rpm might be required.

To avoid the problematic nature of drive cables in catheter blood pumps, some blood pumps have been developed that have a miniature motor that is positioned adjacent to the impeller blades of the pump. In such devices, the motor is implanted in the vascular system or heart along with the pump, and therefore drives the blades directly. See, e.g., U.S. Pat. No. 6,794,789.

But an implantable motor is expensive and complicated, given the extreme miniaturization and wiring/sealing challenges associated with a motor/pump combination that is significantly smaller than the diameter of an average "BB" used in BB guns (i.e., 0.177 inches in diameter). Since these blood pumps are single-use, disposable devices, the high cost of such a miniaturized, implantable motor is particularly disadvantageous.

There is a need, therefore, for a drive cable/catheter assembly that (1) can rotate at speeds well in excess of 20,000 rpm (2) while conforming to an anatomy that includes small-radii bends (3) and can maintain structural integrity for a clinically relevant duration.

SUMMARY OF THE INVENTION

The present invention provides a way to transmit torque at high rpm through portions of mammalian anatomy, which may include twists, turns, or even loops, and to do so for a clinically relevant duration, while avoiding some of the shortcomings of the prior art.

The inventor recognized that a major impediment to the use of a continuous coil for torque transmission at high rotational speeds is the potential for significant vibrations in the coil. In particular, and among other concerns, if the forcing frequency (i.e., the rate at which the motor or other "prime mover"

rotates the coil) is near the natural frequency of the coil (or a harmonic of the natural frequency), large-amplitude vibrations and standing waves will occur. Since the coil would typically be in a catheter or sheath in many medical applications, these vibrations would result in intermittent and spatially irregular contact between the coil and the sheath. Such contact would contribute to system noise, heat generation, and wear that could shorten cable life.

Drive cables in accordance with the present invention are physically adapted to "tune" large-amplitude vibrations, etc., out of the operating drive cable. In other words, the dynamic response of the drive cable is tailored to be damped within the operational regime of interest. This is accomplished by keeping natural frequency of the cable relatively remote from the forcing frequency. Since there is relatively less latitude to vary the forcing frequency due to the requirements of the pump or whatever device is being driven by the transmitted torque, the natural frequency of the cable is advantageously altered, as required, in accordance with the present invention.

Four main parameters contribute to the vibrational characteristics of the drive cable: (1) tension, (2) bending stiffness, (3) linear mass density including localized or point masses, and (4) length. The inventor recognized that by appropriately altering the dynamic characteristics of the drive cable, such as by changing any one or more of the listed parameters, a flexible drive cable could be used to transmit torque at high rpm. As previously indicated, relatively longer-length coils are unsuitable for transmitting torque at rotational speeds in excess of 20,000 rpm. But testing performed by the inventor has revealed that coils are suitable for transmitting torque at speeds well in excess of 20,000 rpm as long as the coil is kept relatively short.

In accordance with the illustrative and some other embodiments of the invention, favorable (i.e., suitable for the operating regime of interest) dynamic characteristics are achieved for a drive cable by using an in-line combination of one or more coils, where needed, and one or more rods, where acceptable. This ensures that drive cables disclosed herein will not incorporate a continuous, un-modified coil in a length that is any longer than is required to accommodate the required harmonic damping and bends in the anatomy.

In the illustrative embodiment, the one or more rod segment(s) and the one or more coil segment(s) are joined end-to-end via any of a variety of techniques for joining such dissimilar elements. The specific location of coils and rods along the drive shaft is dependent upon the required harmonic damping and the anatomy in which the drive cable is used.

Consider, for example, a drive cable in accordance with the illustrative embodiment that is used in conjunction with a blood pump that is to be inserted via the femoral artery. In operation, the blood pump will be positioned in the vascular system along a path defined by the femoral artery, iliac artery, descending aorta, aortic arch, and ascending aorta. (See definitions of the "iliac artery" and "descending aorta" in paragraph 0040.)

In some embodiments, the inventive drive cable will include three rod segments and two coil segments, as follows:
  A first rod segment will transition from an extracorporeal motor to the insertion point at the femoral artery.
  A first coil segment will span the femoral artery and iliac artery, accommodating any curvature.
  A second rod segment will span the descending aorta.
  A second coil segment will span the aortic arch, accommodating its small-radii bend.
  A third rod segment, which couples to the pump shaft, will span the ascending aorta.

In this fashion, for some embodiments, the required harmonic damping and anatomy will determine the appropriate positions of certain cable segments. And again, rods are used where acceptable, and coils are used where required, so that coil segments are no longer than required.

In some other embodiments that are consistent with the illustrative embodiment and that are suitable for use with a blood pump, a drive cable will include one rod segment and two coils segments. The first coil segment will span the extracorporeal motor to the descending aorta. The rod segment will span a portion of or the entire descending aorta. The second coil segment will span the aortic arch and ascending aorta. In this embodiment, therefore, a single rod in the descending aorta provides the required harmonic damping sufficient for the cable/catheter assembly to operate for a clinically relevant duration.

The length of various anatomical features (e.g., femoral artery, descending aorta, etc.) will vary, of course, from person to person as a function of body size and normal anatomical variation. As a consequence, several versions of a drive shaft for use with the blood pump discussed in the example are suitably provided. One is sized for a child, a second is sized for an adolescent, a third is sized for an adult of relatively small stature, and a fourth is sized for an adult of relatively large stature, etc. In some embodiments, all four of such drive cables include the same number and allotment of segments, but the lengths of such segments differ. As a consequence, for these embodiments, the actual position (i.e., distance along the drive shaft) of the various rod segment(s) and coil segment(s) will be different for these different versions of the drive cable.

In some alternative embodiments of a drive cable in accordance with the present teachings, a plurality of relatively short coil segments are attached to one another via collars (e.g., implemented as sections of hypotube, etc.). This configuration is similar to the configuration of the drive cable in the illustrative embodiment in the sense that the collars of the present configuration provide the functionality of the rods. In other words, in these alternative embodiments, the collars provide a dual function—they link adjacent coil sections to one another as well as alter the dynamics of the drive cable in the manner of the stiff rod sections of the previous embodiment.

In some further alternative embodiments, a drive cable incorporates a means for adjusting the relative stiffness or flexibility and/or mass of regions of a continuous drive cable (as opposed to a "composite" rod/coil drive cable or the "segmented-coil" drive cable previously disclosed). This is implemented in some embodiments by, for example, disposing one or more discrete "collars" at various locations along the length of coil. This effectively breaks-up the coil into shorter sections, thereby changing the dynamics of the drive cable. Thus, the dynamic response of a continuous coil can be altered by using:
  a single collar; or
  multiple collars having the same characteristics; or
  multiple collars having varying lengths; or
  multiple collars having varying thicknesses; or
  multiple collars having varying masses; or
  multiple collars having varying stiffness; or
  any combination of the foregoing.

Collars for any of the embodiments described above can be situated externally or internally relative to the coils section(s). In other words, the collars can either be:
  (i) hollow and have an inside diameter that is suitable for receiving, internally, coils segments or rods segments (e.g., to join them, etc.); or (ii) have an outside diameter suitable that enables the collar to be received internally by coils segments or (hollow) rods segments (e.g., to join them, etc.). In other words, the internal collars are used to create a "pin-and-socket" attachment.

Situating the collars within the coil/rod segments reduces the overall diameter of drive cables disclosed herein. For embodiments in which collars are used to alter the relative stiffness or flexibility and/or mass of regions of a continuous (coil) drive cable, the collars will typically, but not necessarily, be situated on the outside of the drive cable.

In yet some further embodiments of a drive cable in accordance with the present teachings, select regions of the coil can be bound together (e.g., soldered, welded, banded, etc.), thereby increasing stiffness and affecting the dynamic characteristics.

In yet some additional embodiments, a machined spring or coil can be formed that has, along its length, variations in material thickness or other properties (material or otherwise) to appropriately tailor dynamic characteristics.

The drive cables described herein are not limited for use in catheter blood pumps. Rather, they are suitable for use in any medical device that requires a torque-transmission cable within a curved portion of the anatomy, such as, for example, within other parts of the vasculature, the gastrointestinal tract, or the spinal canal/ventricular system of the brain. The cables that are disclosed herein are particularly advantageous for use in applications that require a relatively longer cable that is turning at relatively higher rpm in an anatomy that includes relatively smaller-radii bends, since very few if any other drive cables can satisfy such requirements.

BRIEF DESCRIPTION OF THE DRAWINGS

FIG. 2B depicts a drive cable similar to the drive cable of FIG. 2A but having fewer segments.

FIG. 3A depicts a first alternative embodiment of the drive cable that is used in the device of FIG. 1.

FIG. 3B depicts the drive cable of FIG. 3A except that collars for connecting adjacent coil segments are disposed within those segments (i.e., pin-and-socket connection).

FIG. 4 depicts a second alternative embodiment of the drive cable that is used in the device of FIG. 1.

FIG. 5 depicts a third alternative embodiment of the drive cable that is used in the device of FIG. 1

FIG. 7 depicts, via a cross section, a drive cable that is encapsulated in a polymer.

DETAILED DESCRIPTION

Figure 1:
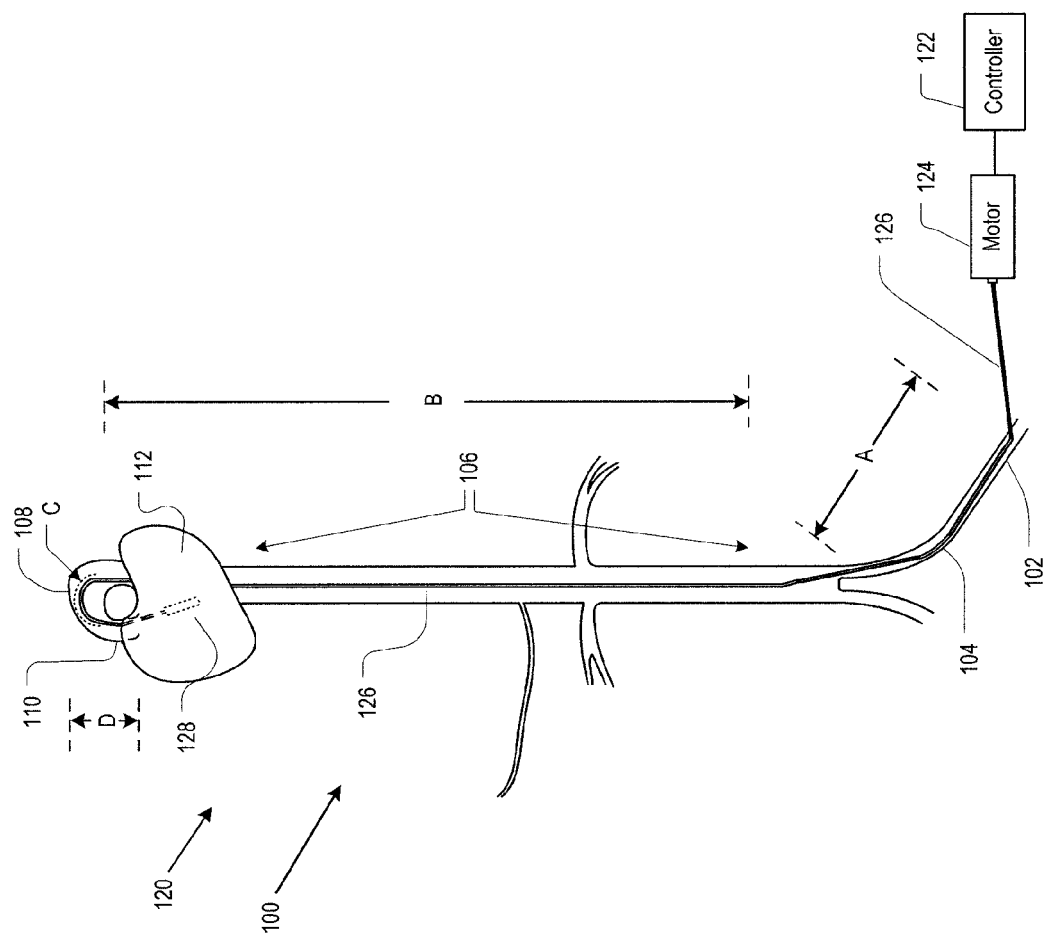
FIG. 1 depicts a cardiac-assist device that incorporates a drive cable in accordance with an embodiment of the present invention, wherein the cardiac-assist device is disposed in the human vascular system and heart.

The following terms and their inflected forms are defined for use in this Specification, including the appended claims:
 i. Axial means an axis or direction that is coincident with a centerline (of a device) and contrary to "radial."
 ii. Bio-compatible means the property of being biologically compatible as determined by accepted medical industry standard.
 iii. Coil is a generally helical element that exhibits good flexibility in bending, is resilient and fatigue resistant. The term "coil" is meant to include uni-filar and multi-filar coils, and also includes multi-layer (i.e., a coil-within-a-coil) arrangements, such as the various coil-within-coil arrangements disclosed in U.S. Pat. No. 6,685,696. Thus, as used herein, a coil-within-coil arrangement is considered to be a single coil.
 iv. Descending aorta means the anatomy defined by the descending thoracic aorta and abdominal aorta,
 v. Discrete means "separate" or "distinct."
 vi. Distal means relatively farther from a first end of a drive cable. The drive cable typically connects a source of torque, (e.g., a motor, etc.) to a user of torque, which is usually a rotatable component, such as a pump assembly or the like. Typically, the source of torque is located at the first (proximal) end of the drive cable and the user of torque is located at the distal end of the drive cable.
 vii. Dynamic Response means the resultant motion (or other output, including sound or heat) of a mechanical element, structure, or system from a mechanical excitation (e.g., rotation, etc.) under specified conditions. For example, vibration, such as the vibration of a cable, is considered to be a dynamic response.
 viii. Forcing Frequency is the frequency at which a system is excited. In rotational systems, the forcing frequency is the rotational speed (e.g., rpm, Hz, radians/second, etc.)
 ix. Harmonic Frequencies are overtones, or integer multiples of the natural frequency.
 x. Harmonic Resonance is an undesirable condition wherein the forcing frequency and the natural frequency (or harmonic frequencies) are equal or close in magnitude. The amplitude of oscillation and energy exchanged (between potential and kinetic) are an appreciable fraction of the maximum. This condition results in undesirable noise, wear and heat generation.
 xi. Iliac artery means the anatomy defined by the external iliac artery and the common iliac artery.
 xii. Natural Frequency means a frequency at which a system oscillates or vibrates if it is disturbed.
 xiii. Operatively coupled means that the operation of one device affects another device. For example, if a drive cable is "operatively coupled" to an impeller of a pump, it is capable of driving the impeller (i.e., causing the impeller to rotate). Operatively coupled devices need not be directly physically coupled.
 xiv. Physically coupled means direct, physical contact between two objects (e.g., two surfaces that abut one another, etc.).
 xv. Proximal means relatively closer to the first end of the drive cable.
 xvi. Proximate means "near to."
Other definitions may be provided later in this disclosure.

FIG. 1 depicts heart 112 and a portion of human vascular system 100; in particular, femoral artery 102, iliac artery 104, descending aorta 106, aortic arch 108, and ascending aorta 110. FIG. 1 also depicts cardiac-assist device 120 that is deployed in vascular system 100 and heart 112.

The cardiac-assist device 120 comprises controller 122, motor 124, drive cable 126, and pump assembly 128. In use, some elements of cardiac-assist device 120 are extracorporeal (i.e., remain outside of the patient) and others are located within the patient's body. More specifically, controller 122, motor 124, and some of drive cable 126 remain outside of the body while, when deployed, much of the drive cable and all of pump assembly 128 are located within the body.

To maintain a focus on issues that are germane to an understanding of the present invention, only brief mention will be made of elements of cardiac-assist device 120 other than drive cable 126. Further disclosure concerning such other elements of a cardiac-assist device can be found, for example, in co-pending U.S. patent application Ser. Nos. 11/565,969 and 11/565,970.

Controller 122 is the human interface of cardiac-assist device 120. The controller, which incorporates a microprocessor, typically provides control and monitoring functions. Motor 124 is the prime mover that drives pump assembly 128.

Pump assembly 128 includes a rotating impeller (not depicted) that is capable of supplementing native cardiac output by inducing flow through the pump. Drive cable 126 operatively couples motor 124 to pump assembly 128, thereby transmitting motor torque to the pump assembly to drive the impeller. Drive cable 126 will typically rotate at a speed well in excess of 1000 rpm and possibly as high as 100,000 rpm.

In some embodiments, known catheterization techniques (e.g., Seldinger, etc.) are used to percutaneously introduce pump assembly 128 into femoral artery 102 and advance it through iliac artery 104, descending aorta 106, around aortic arch 108, and then to its intended placement site. A variety of placement sites are possible; typical sites include ascending aorta 110 and within heart 112 (e.g., across the aortic valve, within the left ventricle, etc.). Other sites may be possible as well (e.g., in descending thoracic aorta, in suitably-sized peripheral blood vessels, or in the right side of the heart or in right-side-related vasculature).

FIGS. 2A through 5 depict several embodiments of drive cable 126, identified as drive cables 126A, 126B, 126C, and 126D. In all of these embodiments, the drive cables include physical adaptations that are intended to tune out large-amplitude vibrations and provide harmonic damping in the desired operating regime. Broadly defined, the desired operating regime is between about 1000 rpm and about 100,000 rpm. The desired operating regime will more typically fall between about 20,000 rpm to 100,000 rpm, and most likely be within the range of about 30,000 rpm to about 80,000 rpm.

Figure 2A:
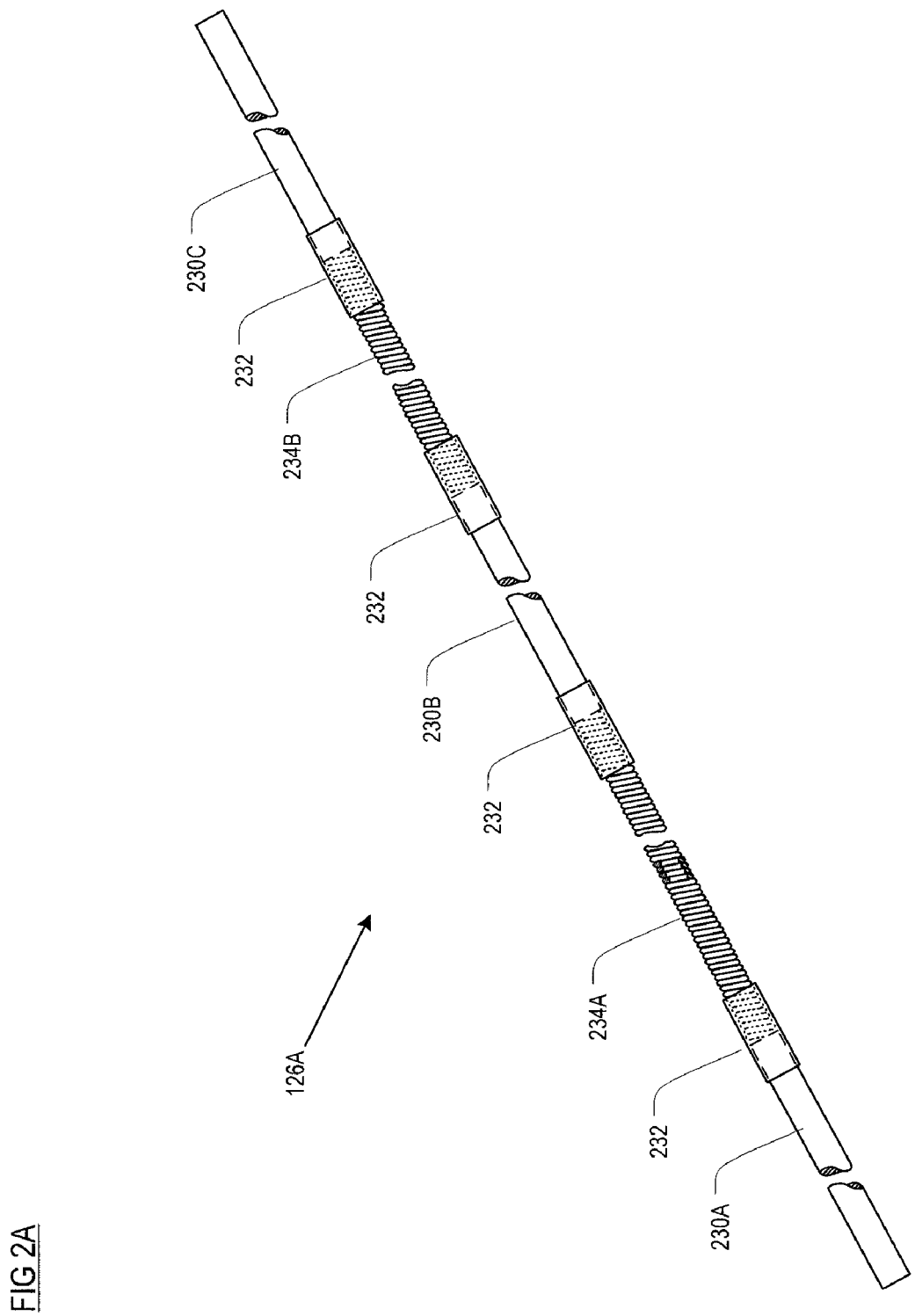
FIG. 2A depicts the illustrative embodiment of the drive cable that is depicted in FIG. 1.

Turning now to FIG. 2A, drive cable 126A comprises a plurality of discrete segments, and is therefore referred to as a "composite" drive cable. By way of illustration, but not limitation, drive cable 126A depicted in FIG. 2A includes five discrete segments 230A, 230B, 230C, 234A, and 234B. The segments are coupled end-to-end, thereby forming a linear arrangement. Some other embodiments of drive cable 126A in accordance with the illustrative embodiment of the present invention will have fewer than five discrete segments (see, e.g., FIG. 2B) and still further embodiments will have more than five discrete segments (see, e.g., FIG. 6). As discussed further below, the specific number of discrete segments that are included in drive cable 126A, and the position of such segments along the cable, is related to the required harmonic damping and the anatomy in which drive cable 126A is being used.

The five discrete segments of composite drive cable 126A of FIG. 2A can be classified as being associated with one or the other of at least two segment types or groups. Segments 230A, 230B, 230C (generically or collectively referenced "segment[s] 230") belong to a first group. Segments 234A and 234B (generically or collectively referenced "segment[s] 234") belong to a second group. The segments in the first group differ from those in the second group in terms of structural configuration.

The phrase "structural configuration" is used herein to refer to the structural arrangement of the segment. Examples of a "structural configuration" include, without limitation, a rod, a coil, a bellows, and the like. The phrase "structural configuration," as used in this description and in the appended claims, is not intended to refer to segment attributes or characteristics such as the thickness, mass, diameter or length of a segment.

Each of segments 230 in the first group of segments has a structural configuration that is stiff, both in torsion and in bending, and is therefore stiff in torsional and planar vibration. In the illustrative embodiment, segments 230 are configured as a "rod." It should be understood that stiff segments 230 are flexible enough to pass atraumatically through the sometimes tortuous anatomy of a natural body lumen, cavity, vessel, orifice and the like.

In some embodiments, stiff segments 230 are solid. In some additional embodiments, stiff segments 230 are hollow. In some further embodiments, drive cable 126A will include some solid, stiff segments as well as some hollow, stiff segments. Whether solid or hollow, a rod is well suited for transmitting torque at high rpm (in excess of 20,000 rpm). More particularly, by virtue of its structure, a segment configured as a rod can withstand high levels of torque without fracturing or otherwise losing structural integrity.

There is, however, a caveat to the use of stiff segments as torque transmitters. And that is that while rotating during normal operation these stiff segments must remain substantially straight. If a stiff segment were to rotate while bent, such as might be required to accommodate the anatomy, its ability to transmit torque at high rpm and maintain structural integrity would be substantially compromised. In fact, if a drive cable that included stiff segment(s) 230 were situated in a system that required the stiff segment to be radically bent while rotating, such as to negotiate a 45-degree bend, it is likely that the segment would experience structural failure soon after coming up to rotational speed (or even before reaching its rated rpm).

Each of the segments 234 in the second group has a structural configuration that renders it flexible enough to rotate while conforming to a curved path. In the illustrative embodiment, segments 234 are configured as coils, which are preferably, but not necessarily, hollow (i.e., have lumens). Compared to a rod configuration, a straight section of coil has a substantially decreased ability to withstand the stresses that result from transmitting torque at high rpm. But a bent section of coil has a substantially greater ability than a rod to withstand the stresses that result from transmitting torque at high rpm around a corner or bend. Thus, flexible segments 234 have a greater capacity for transmitting torque at high rpm along a curved path than rod segments 230. It is notable that even if a rod were formed from a super-elastic substance, such as Nitinol, it would not be able to operate long term in a system having small-radii bends.

In various embodiments, coil segments 234 can be a single coil or multi-layer (i.e., a coil-within-a-coil), such as the various coil-within-coil arrangements disclosed in U.S. Pat. No. 6,685,696. Additionally, in some embodiments, the coils are uni-filar and in some other embodiments, they are multi-filar.

Composite drive cable 126A therefore comprises a linear arrangement or in-line alternating combination of discrete stiff (e.g., rod, etc.) segments 230 and discrete flexible (e.g., coil, etc.) segments 234. The discrete segments that form drive cable 126A must, of course, be joined to one another. The segments can be joined by any of variety of known techniques for joining dissimilar elements. For example, segments can be joined by using adhesives, pin-and-socket construction, swaging, brazing, welding, soldering, or combinations thereof.

In the illustrative embodiment that is depicted in FIG. 2A, segments 230 and 234 are joined by fitting a tube or "collar" 232 over opposed ends of adjacent segments and then swaging the tube to those segments. Adhesive is typically (but not necessarily) used in conjunction with swaging to enhance joint strength and durability.

Segments 230 and 234 can be formed from a wide variety of materials. For example, and without limitation:
- stiff segments 230 are suitably formed from materials such as nickel titanium super-elastic shape memory alloy (Nitinol), stainless steel, MP-35 alloy (chromium/nickel/molybdenum/cobalt), various other metals and metal alloys;
- flexible segments 234 are suitably formed from materials such as stainless steel, MP-35, or other metals and metal alloys; and
- tubes/collars 232 are suitably formed from stainless steel hypotube, plastics, and the like.

In some embodiments, one or more stiff segments 230 are tapered or stepped. This will vary stiffness, etc. Furthermore, to the extent that stiff segments 230 and flexible segments 234 may have different diameters, the stiff segments can be stepped to match the diameter of the coil segments. Steps are advantageously radiused to minimize stress concentration at a step.

As previously indicated, in accordance with the present teachings, drive cable 126A is advantageously configured for use in conjunction with a specific system. The particular number, location, and length of specific stiff segments 230 and flexible segments 234 will, therefore, be functions of the required harmonic damping and the anatomy.

Referring again to FIG. 1, consider the anatomy of the path leading from femoral artery 102 to heart 112 in the human vascular system. Starting at the upper thigh, femoral artery 102 curves as it becomes iliac artery 104 and then connects to descending aorta 106. Proceeding toward heart 112, descending aorta 106 is relatively straight. There is a sharp bend at aortic arch 108; this vascular feature is roughly a 180-degree arc on a 1.5 inch radius. Aortic arch 108 leads to ascending aorta 110.

So, in some embodiments in which composite drive cable 126A is to be used in conjunction with cardiac-assist device 120, the drive cable includes:
- at least two flexible sections (i.e., one to accommodate bending between femoral artery 102 and descending aorta 106 and the second to negotiate aortic arch 108); and
- at least three stiff sections (i.e., one to extend from motor 124 to a certain point in femoral artery 102, a second for placement in descending aorta 106, and a third for placement in ascending aorta 110).

The stiff sections will be implemented as rods and the flexible sections will be implemented as coils. The general approach is to provide flexible segments where required and stiff segments where permissible, as a function of the required harmonic damping as well as the anatomy in which composite drive cable 126A is being used.

Of course, the specific position along composite drive cable 126A at which any particular segment begins and ends is a function of the required harmonic damping and anatomy. In the case of the femoral path to the heart depicted in FIG. 1, in some embodiments, the various segments have a size that typically (but not necessarily) falls in the following ranges:

First flexible segment (i.e., 234A in FIG. 2) has a length A that is typically within a range of about 10 centimeters to about 90 centimeters.

Second flexible segment 234B has a length C that is typically within a range of about 5 centimeters to 25 centimeters.

First stiff segment (i.e., 230A), which is at least partially extra-corporeal, will typically be about 5 centimeters to about 25 centimeters.

Second stiff segment (i.e., 230B) has a length B that is typically within a range of about 10 centimeters to about 90 centimeters.

Third stiff segment (i.e., 230C) has a length D that is typically in a range of about 5 centimeters to about 15 centimeters.

It will be appreciated that the distances and the lengths of the various segments, as provided above, depend upon the required harmonic damping and the anatomy of the patient. The anatomy will, of course, be dictated by the patient's size, age, and gender, as well as other factors. It will be understood, therefore, that the length of any given segment 230 or 234, as provided above, may be significantly outside the stated ranges, as a function of required harmonic damping and anatomical variation. An illustrative embodiment of cable 126A, for use in conjunction with cardiac-assist device 120 via femoral insertion, is provided in Table 1A below:

TABLE 1A

Embodiment of Drive Cable 126A that is Suitable for use in conjunction with a Cardiac-Assist Device

| SEGMENT POSITION IN CABLE | TYPE | LOCATION CM ALONG CABLE START | LOCATION CM ALONG CABLE END | LOCATION IN VASCULAR SYSTEM |
|---|---|---|---|---|
| 1 | Stiff (ROD) | 0 | 15 | Extracorporeal to Femoral Artery |
| 2 | Flexible (COIL) | 15 | 65 | Femoral Artery to Descending Aorta |
| 3 | Stiff (ROD) | 65 | 110 | Descending Aorta |
| 4 | Flexible (COIL) | 110 | 125 | Aortic arch |
| 5 | Stiff (ROD) | 125 | 135 | Ascending aorta |

FIG. 2B depicts a variation of drive cable 126A, wherein the drive cable includes less than five discrete segments. More particularly, in the embodiment of drive cable 126A that is depicted in FIG. 2B, the drive cable comprises three segments: one rod segment 230D that is flanked by two coils segments 234C and 234D. Like the illustrative embodiment that is depicted in FIG. 2A, the various segments of the drive cable that are depicted in FIG. 2B are joined via collars 232. This embodiment of drive cable 126A is also intended for use in conjunction with cardiac-assist device 120 via femoral insertion, among any other uses.

TABLE 1B

Variation of Drive Cable 126A, as depicted in FIG. 2B

| SEGMENT POSITION IN CABLE | TYPE | LOCATION CM ALONG CABLE START | LOCATION CM ALONG CABLE END | LOCATION IN VASCULAR SYSTEM |
|---|---|---|---|---|
| 1 | Flexible (COIL) | 0 | 65 | Extracorporeal to Descending Aorta |
| 2 | Stiff (ROD) | 65 | 75 | Descending Aorta |

TABLE 1B-continued

Variation of Drive Cable 126A, as depicted in FIG. 2B

| SEGMENT POSITION IN CABLE | TYPE | LOCATION CM ALONG CABLE | | LOCATION IN VASCULAR SYSTEM |
|---|---|---|---|---|
| | | START | END | |
| 3 | Flexible (COIL) | 75 | 135 | Descending Aorta to Ascending Aorta |

Table 1B, above, provides additional detail of the variation of drive cable 126A that is depicted in FIG. 2B. The distances and the lengths of the various segments in drive cable 126A, as provided in Table 1B, are provided by way of illustration, not limitation. It is to be understood that a three-segment drive cable can be implemented with segments having different lengths than those indicated in Table 1B. In particular and as previously disclosed, the specific lengths of the various segments of drive cable 126A depend upon the required harmonic damping and the anatomy of the patient.

FIG. 3A depicts drive cable 126B. Drive cable 126B comprises a plurality of short, flexible segments, which are implemented in the embodiment that is depicted in FIG. 3 as coils $334i$, i=1, n (segments 334A, 334B, 334C, and 334n are shown). Coils $334i$ can be uni-filar or multi-filar. The flexible segments are joined to one another by collars 332, which can be implemented in the same fashion and use the same methods for joining as described for previous embodiments.

Drive cable 126B is typically coupled, at its two ends, to rigid shafts, etc. These shafts (e.g., shaft 330 and shaft 336) are typically associated with (1) a prime mover and (2) the device that uses the torque that is provided by the prime mover. For example, in the case of a cardiac-assist device, in some embodiments, shaft 330 extends from the motor and shaft 336 extends from the pump. In such embodiment, shafts 330 and 336 are not considered to be a part of drive cable 126B.

In some embodiments, rod 330 is not part of the prime mover; rather, rod 330 is simply the first segment of drive cable 126B. In a medical application, for example, rod 330 would typically (but not necessarily) be extracorporeal. In particular, in the case of a drive cable for a cardiac-assist device, it can be advantageous for extracorporeal portions of the drive cable to be a rod as long as there is no requirement for it to bend sharply. As previously discussed, a rod can handle much higher rotational speeds and torque along a straight line, and is therefore better suited for such service. In some further embodiments, rod 336 is part of drive cable 126B.

Unlike drive cable 126A, drive cable 126B does not include one or more discrete, relatively long rod segments interspersed among coil segments. As a consequence, the layout of drive cable 126B is not dependent upon the geometry of the anatomy to the same extent as drive cable 126A. That is, compared to drive cable 126A, the nominal arrangement or layout of drive cable 126B accommodates more anatomical variations.

In some embodiments, the length of each coil $334i$ within drive cable 126B is the same. In some other embodiments, the lengths of the various coils within drive cable 126B are not equal. In all of these embodiments, the length of coil segments $334i$ will depend, to some extent, upon the forcing frequency (e.g., the speed at which a motor or other prime mover is intended to turn the drive cable). Acceptable length(s) for coil segments $334i$ can be determined either empirically or analytically.

Regarding an analytical approach, the equations that approximate the dynamic response of any particular embodiment of drive cable 126 (i.e., drive cable 126A, 126B, etc.) can be developed by those skilled in the art. Having an understanding (i.e., a mathematical characterization) of the dynamic response of a given drive cable, knowing the details of the forcing frequency, and in conjunction with this disclosure, those skilled in the art will be able to provide a design for drive cable 126B (e.g., determine coil length, determine coil stiffness, etc.) that tunes out large amplitude vibrations, in accordance with the invention.

FIG. 3B depicts an embodiment of a drive cable wherein collars 333 that connect adjacent coil segments (e.g., coil segments 334A and 334B) or adjacent coil and (hollow) rod segments (e.g., rod segment 330 and coil segment 334A) are disposed inside the coils (or coil and rod). It is notable that for this embodiment, the gap that appears between coil segments 334A and 334B would not be present; this is simply for illustrative purposes to demarcate the ends of these adjacent coil segments.

The use of internally-disposed collars 333 in FIG. 3B illustrates a "pin-and-socket" connection. For such embodiments, the outside diameter of collars 333 is typically sized to provide a tight fit within the coils (or rods). Additionally, adhesive, etc., can be used to bind the collars to the segments that are being joined. In comparison to externally-disposed collars, the use of internally-disposed collars will typically reduce the (maximum) outside diameter of a drive cable in accordance with the present teachings.

FIG. 4 depicts another embodiment of a drive cable in accordance with the present teachings: drive cable 126C. This drive cable includes an unbroken, long coil 434 rather than a plurality of coil segments (although coil 434 can be uni-filar or multifilar). As with drive cable 126B, the ends of drive cable 126C will typically couple to rods 430 and 436 that might or might not be considered to be a part of the drive cable (e.g., in some embodiments, these rods will be a part of the prime mover and/or torque user and not a part of drive cable 126C, proper. Alternatively, the proximal end, distal end, or any intermediate region(s) of coil 434 can be fused together to provide the dynamic characteristics of a rod.

Drive cable 126C includes a plurality of collars $432i$, depicted in FIG. 4 as collars 432A, 432B, 432C, 432D, and 432E.

Collar 432A is used to couple rods 430 and 436 to the coil 434. The four other collars (collars 432B, 432C, 432D, and 432E) which each have a different length, thickness, shape, mass, and stiffness, are used to alter the dynamic response of coil 434. The collars effectively segregate coil 434 of drive cable 126C into a plurality of coil segments, akin to drive cable 126B. Collars $432i$ can be "slid" over coil 434 or formed in place around coil 434 in known fashion (e.g., fusing two collar "halves" together, etc.).

In further detail, collars 432C and 432B have the same thickness as one another but are of different lengths. When positioned on drive cable 126C in the same location, collar 432C would have the effect of stiffening the drive cable more than collar 432B. It would also add more mass to the cable and would stiffen a greater length of the drive cable.

Collar 432D is thicker than either of collars 432B or 432C, and would stiffen drive cable 126C even further. Furthermore, collar 432D will provide an ability to concentrate more mass (than either of collars 432B or 432C) at a given location.

Collar 432E has a tapered geometry that can further enhance stiffening and mass concentration, even relative to collar 432D.

The specific placement of any of these collars is an additional parameter that is used to tailor the dynamic response of drive cable 126C, as a function of its intended operating regime.

The embodiment of drive cable 126C that is depicted in FIG. 4 includes four "dynamics-affecting" collars of different types. It is to be understood, however, that embodiments of drive cable 126C are not limited to four such collars.

For example, some embodiments of drive cable 126C include less than four collars. In fact, some embodiments will include only a single collar. And that single collar can be configured as any of the collars 432B through 432E that are depicted in FIG. 4. Furthermore, a single collar having other specific configurations that are not depicted herein but will be known or otherwise occur to those skilled in the art after reading the present disclosure may suitably be used.

In some other embodiments, drive cable 126C includes more than four "dynamics-affecting" collars. In some such embodiments, all collars within a given embodiment of drive cable 126C will be the same type (e.g., all 432B, etc.) In yet some further embodiments, drive cable 126C will include plural collars of at least two different types (e.g., some are 432B and some others are 432D, and so forth). It is to be understood that the number of dynamics-affecting collars and their specific "type" are freely permutable to tune the dynamic response of drive cable 126C as dictated by application specifics (i.e., system geometry, forcing frequency, etc.).

FIG. 5 depicts drive cable 126D, which is another embodiment of a drive cable in accordance with the present teachings. This drive cable includes a single, long machined coil 534 (although coil 534 can be uni-filar or multifilar). Like drive cables 126B and 126C, the ends of drive cable 126D will typically couple to rods (not depicted) that might or might not be considered to be a part of the drive cable (e.g., in some embodiments, these rods will be a part of the prime mover and/or torque user and not a part of drive cable 126D, proper.) In yet some additional embodiments, the proximal and distal ends of machined coil 534 are machined to be suitably stiff so as to provide the functionality of a rod.

In accordance with this embodiment, the thickness or other material properties of machined coil 534 are varied along its length to appropriately tailor its dynamic characteristics to a desired operating regime. Unlike a coil that is formed by a winding process, a machined or laser-cut coil can be fabricated with a greater degree of precision to include any of a number of structural variations.

For example, in the embodiment depicted in FIG. 5, coil 534 includes two sections 537 and 539 having a first "material" width and section 538 having a second "material" width.

The phrase "material width" is meant to indicate the width of the material that forms the coil, as opposed to the width or diameter of the coil itself. As depicted in FIG. 5, the first material width is relatively narrower than the second material width. In the absence of any other differences between these sections, section 538 will be relatively stiffer than sections 537 and 539. For simplicity, coil 534 in FIG. 5 includes only three sections having two different material widths. It will be appreciated that, as required, coil 534 can be machined to vary in other ways and on a more frequent basis.

Figure 6:
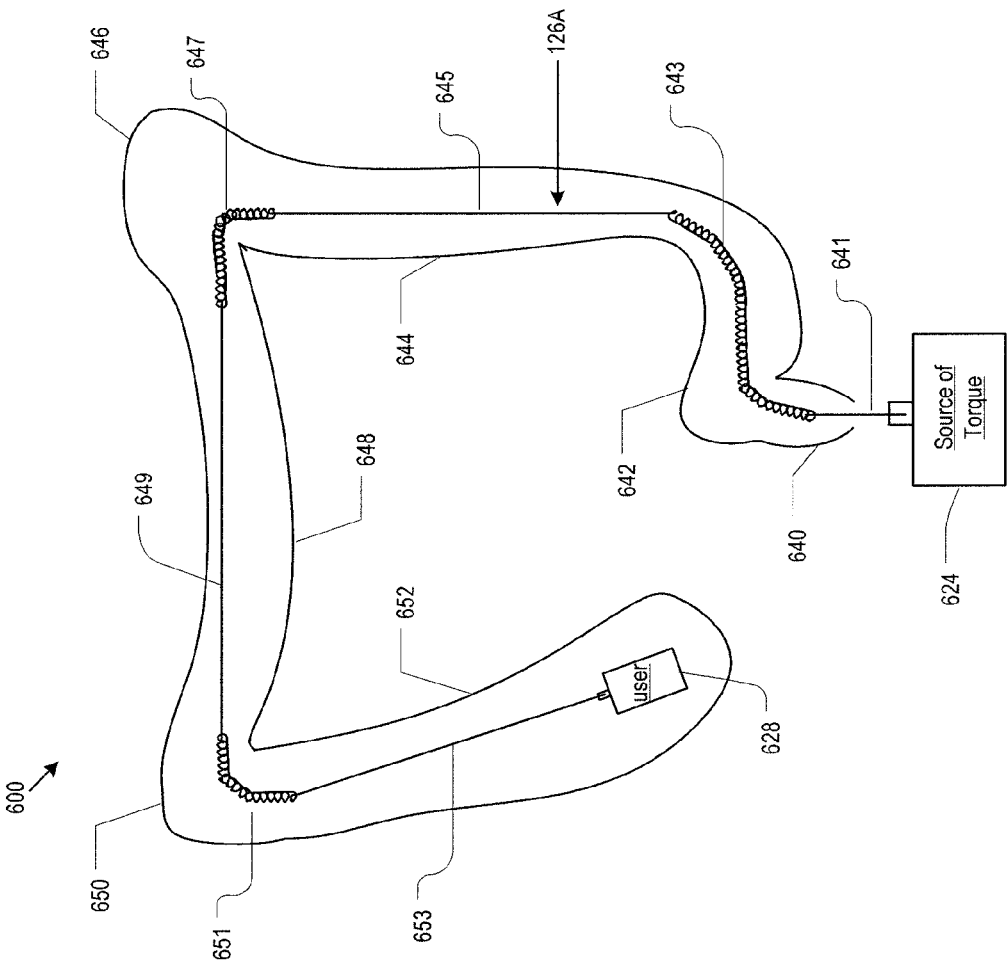
FIG. 6 depicts a drive cable similar to the drive cables of FIGS. 2A and 2B being used in conjunction with a hypothetical medical device deployed within the rectum and colon.

FIG. 6 depicts a hypothetical device in rectum and colon ("R&C") 600. The device includes source of torque 624, drive cable 126A, and user of torque 628. Source 624 is operatively coupled to the proximal end of cable 126A and torque user 628 is operatively coupled to the distal end of cable 126A. The drive cable transmits torque from source 624 to user 628.

As depicted in FIG. 6, the anatomy of R&C 600 is defined by various straight and curved sections. In particular, R&C 600 includes relatively straight extracorporeal portion and rectum 640, "s-curved" sigmoid colon 642, relatively straight descending colon 644, curved splenic flexure 646, relatively straight transverse colon 648, curved hepatic flexure 650, and straight ascending colon 652. The lengths of these various anatomical regions can vary greatly, depending upon patient gender, age, and other factors. For this anatomy, drive cable 126A can be organized as listed in Table 2, below. The implied lengths of the particular segments are provided by way of illustration, not limitation, and can vary significantly, of course, as a function of the required harmonic damping and individual anatomy.

TABLE 2

Embodiment of a Drive Cable Suitable for use in R&C 600 of FIG. 6

| ANATOMY SECTION | SECTION DESCRIPTION | DRIVE CABLE SEGMENT | SEGMENT TYPE | SEGMENT POSITION IN DRIVE CABLE | LOCATION (CM ALONG CABLE) START | END |
|---|---|---|---|---|---|---|
| 640 | STRAIGHT | 641 | STIFF | 1 | 0 | 25 |
| 642 | CURVED | 643 | FLEXIBLE | 2 | 25 | 65 |
| 644 | STRAIGHT | 645 | STIFF | 3 | 65 | 90 |
| 646 | CURVED | 647 | FLEXIBLE | 4 | 90 | 110 |
| 648 | STRAIGHT | 649 | STIFF | 5 | 110 | 150 |
| 650 | CURVED | 651 | FLEXIBLE | 6 | 150 | 170 |
| 652 | STRAIGHT | 653 | STIFF | 7 | 170 | 185 |

It is assumed that the drive cable in FIG. 6 is required to rotate at high rpm to transmit torque from source 624 to user 628. Therefore, a drive cable suitable for such service, such as embodiments of drive cable 126 disclosed herein, is advantageously used. For this particular example, drive cable 126A is used; embodiments of drive cables 126B, 126C, or 126D can suitably be used as well.

For use in the human body, most embodiments of drive cable 126 (e.g., drive cable 126A, 126B, 126C, 126D etc., will be constrained by a catheter or other sheath. The sheath will be bio-compatible, capable of being pushed (through a vascular system, etc.) and flexible, to negotiate the anatomy. For use in the vasculature, the sheath must be effective in preventing fluid exchange between the bloodstream and the interior of the sheath (i.e., the sheath's lumen), from full vacuum to about 20 atmospheres internal pressure. When used in the vasculature, the size of the sheath is constrained to an outer diameter of less than about 30 Fr (10 millimeters).

Since drive cable 126 will impinge upon the sheath intermittently, if not continuously, there should be low friction at this interface. This can be accomplished by forming the sheath from a suitable polymer, elastomer, fluoropolymer, or thermoplastic material. Examples of such materials include, without limitation, PTFE (polytetrafluoroethylene, commonly known by the trademark Teflon®, available from Dupont), FEP (fluorinated ethylene propylene), ETFE (a polymer of tetrafluoroethylene and ethylene), PFA (perfluoroalkoxy copolymer resin), PP (polypropylene), PE (polyethylene), silicone rubber, PU (polyurethane), PVC (polyvinyl chloride), Pebax® (polyether block amides are plasticizer-free thermoplastic elastomers available from Arkema, Inc.), UHMWPE (ultra-high molecular weight polyethylene), Hytrel® (thermoplastic polyester elastomers available from Dupont), Polyimide, and combinations or layers thereof.

Drive cables, as disclosed herein and used throughout industry, are constructed primarily of metals because metals have favorable fatigue properties and elastic moduli. In some embodiments, the various embodiments of drive cable 126 (e.g., drive cables 126A, 126B, 126C, and 126D, etc.) are encapsulated in material 750, such as depicted in FIG. 7.

Among other benefits, the encapsulating material, which is softer than metal, attenuates the impact of collisions between the drive cable and the sheath. This impact attenuation is expected to reduce the noise and perceptible vibration that is generated by the system. Additionally, the encapsulation is expected to provide a slight increase to the bending stiffness of the encapsulated member, which will alter the dynamic response (e.g., harmonic behavior, etc.) of the drive cable.

Materials that are suitable for encapsulating the drive cable include, without limitation: elastomer, fluoropolymer, or thermoplastic material. Examples of such materials include, without limitation, PTFE (polytetrafluoroethylene, commonly known by the trademark Teflon®, available from Dupont), FEP (fluorinated ethylene propylene), ETFE (a polymer of tetrafluoroethylene and ethylene), PFA (perfluoroalkoxy copolymer resin), PP (polypropylene), PE (polyethylene), silicone rubber, PU (polyurethane), PVC (polyvinyl chloride), Pebax® (polyether block amides are plasticizer-free thermoplastic elastomers available from Arkema, Inc.), UHMWPE (ultra-high molecular weight polyethylene), Hytrel® (thermoplastic polyester elastomers available from Dupont), Polyimide, and combinations or layers thereof.

Encapsulation processes include the use of shrink tubing and/or adhesive bonding as well as other processes known to those skilled in the art.

Thus, a drive cable in accordance with the present teachings can be used to form a drive connection from a prime mover or source of torque to a blood pump, or for other medical applications that might employ a working head, cutter member, or the like.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. An article comprising a system-specific rotary drive cable that, in operation, is rotated at a rate of at least 1000 rpm to drive a rotatable element of the article, wherein the rotary drive cable is designed for use in a system that includes a first section and a second section through which at least a portion of the rotary drive cable must traverse to position the rotatable element in an operational location in the system, wherein the first section of the system is relatively straight compared to the second section of the system, and the second section is relatively bent compared to the first section, and further wherein:
   (a) the drive cable comprises a plurality of discrete segments that are coupled end to end;
   (b) the plurality of segments comprises a first rod and a first coil;
   (c) a first location of the first rod and a second location of the first coil along the drive cable are a function of:
      (i) a distance between the first section and the second section of the system; and
      (ii) a distance between the second section of the system and the operational location, so that when the rotatable element is in the operational position in the system, the first rod is within the first section of the system and the first coil is in the second section of the system.

2. The article of claim 1 wherein the plurality of segments further includes a second rod, a third rod, and a second coil, and wherein the segments are arranged serially along the drive cable as follows: first rod, first coil, second rod, second coil, third rod.

3. The article of claim 2 wherein a length of the first rod is with a range of about 5 centimeters to about 25 centimeters.

4. The article of claim 2 wherein a length of the first coil is with a range of about 10 centimeters to about 90 centimeters.

5. The article of claim 2 wherein a length of the second rod is with a range of about 10 centimeters to about 90 centimeters.

6. The article of claim 2 wherein a length of the second coil is with a range of about 5 centimeters to about 25 centimeters.

7. The article of claim 2 wherein a length of the third rod is with a range of about 5 centimeters to about 15 centimeters.

8. The article of claim 1 further comprising a motor, wherein a first end of the drive cable is operatively coupled to the motor.

9. The article of claim 1 further comprising an impeller, wherein a second end of the drive cable is operatively coupled to the impeller.

10. An article comprising a system-specific rotary drive cable that is rotated at a rate of at least 1000 rpm to drive a rotatable element of the article, wherein the drive cable comprises a plurality of segments disposed in a linear arrangement, wherein:
    (a) the segments comprise one or more segments of a first type and one or more segments of a second type;
    (b) segments of the first type possess a relatively greater capacity for transmitting torque along a curved path than segments of the second type;
    (c) a position of the segments in the linear arrangement thereof is selected to correspond to a geometry of a system in which the drive cable is used, wherein segments of the first type are positioned to coincide with relatively more curved regions of the system and segments of the second type are positioned to coincide with relatively less curved regions of the system when the rotatable element is at an operational location in the system.

11. The article of claim 10 wherein the segments of the first type comprise a coil.

12. The article of claim 10 wherein the segments of the first type have a different structural configuration than the segments of the second type.

13. The article of claim 10 wherein in the linear arrangement, the segments of the first type alternate with segments of the second type.

14. The article of claim 10 further comprising a motor, wherein a first end of the drive cable is operatively coupled to the motor.

15. The article of claim 10 further comprising an impeller, wherein a second end of the drive cable is operatively coupled to the impeller.

* * * * *